(12) United States Patent
Kermani et al.

(10) Patent No.: US 9,052,278 B2
(45) Date of Patent: Jun. 9, 2015

(54) SYSTEM AND METHOD FOR MEASURING AN ANALYTE IN A SAMPLE

(75) Inventors: Mahyar Z. Kermani, San Ramon, CA (US); Maria Teodorczyk, San Jose, CA (US)

(73) Assignee: Cilag GmbH International, Zug (CH)

( * ) Notice: Subject to any disclaimer, the term of this patent is extended or adjusted under 35 U.S.C. 154(b) by 327 days.

(21) Appl. No.: 13/810,639

(22) PCT Filed: Jul. 18, 2011

(86) PCT No.: PCT/US2011/044385
§ 371 (c)(1),
(2), (4) Date: May 8, 2013

(87) PCT Pub. No.: WO2012/012341
PCT Pub. Date: Jan. 26, 2012

(65) Prior Publication Data
US 2013/0220836 A1    Aug. 29, 2013

Related U.S. Application Data

(60) Provisional application No. 61/365,719, filed on Jul. 19, 2010, provisional application No. 61/366,099, filed on Jul. 20, 2010, provisional application No. 61/442,664, filed on Feb. 14, 2011.

(51) Int. Cl.
*G01N 27/327* (2006.01)
*A61B 5/145* (2006.01)
*G01N 27/416* (2006.01)

(52) U.S. Cl.
CPC .......... *G01N 27/327* (2013.01); *A61B 5/14532* (2013.01); *A61B 2560/0204* (2013.01); *A61B 2560/0223* (2013.01); *A61B 2560/0252* (2013.01); *A61B 2562/0295* (2013.01); *G01N 27/416* (2013.01); *G01N 27/3273* (2013.01)

(58) Field of Classification Search
CPC   G01N 27/327; G01N 27/3273; G01N 27/416
See application file for complete search history.

(56) References Cited

U.S. PATENT DOCUMENTS

| 5,942,102 | A | 8/1999 | Hodges et al. |
| 6,413,410 | B1 | 7/2002 | Hodges et al. |
| 6,780,645 | B2 | 8/2004 | Hayter et al. |
| 7,749,371 | B2 | 7/2010 | Guo et al. |
| 2004/0099540 | A1* | 5/2004 | Neel et al. ...................... 205/792 |

(Continued)

FOREIGN PATENT DOCUMENTS

| CN | 201481420 U | 5/2010 |
| CN | 201508361 U | 6/2010 |

(Continued)

OTHER PUBLICATIONS

Patent Examination Report issued in related Australian Patent Application No. 2011279872, dated Mar. 3, 2014, 3 pages.

(Continued)

*Primary Examiner* — Jennifer Dieterle

(57) ABSTRACT

Described are methods and systems to calculate an analyte concentration of a sample are provided without temperature compensation to a glucose concentration calculation when a measured or sampled current is taken at or before a change in a first voltage to a second voltage that are applied to a test trip with electrodes in a test cell.

9 Claims, 11 Drawing Sheets

(56) References Cited

U.S. PATENT DOCUMENTS

| | | |
|---|---|---|
| 2005/0258034 A1 | 11/2005 | Iketaki et al. |
| 2007/0227912 A1 | 10/2007 | Chatelier et al. |
| 2007/0235347 A1 | 10/2007 | Chatelier et al. |
| 2009/0026094 A1 | 1/2009 | Deng et al. |
| 2009/0084687 A1 | 4/2009 | Chatelier et al. |
| 2009/0184004 A1 | 7/2009 | Chatelier et al. |
| 2009/0208734 A1 | 8/2009 | Macfie et al. |
| 2009/0301899 A1 | 12/2009 | Hodges et al. |

FOREIGN PATENT DOCUMENTS

| | | | |
|---|---|---|---|
| JP | 2007271622 A | | 10/2007 |
| JP | 2009085950 A | | 4/2009 |
| JP | 2009294213 A | | 12/2009 |
| WO | WO 2008/040998 | * | 4/2008 |
| WO | WO 2008/040998 A2 | | 4/2008 |
| WO | WO 2009/041782 A2 | | 4/2009 |

OTHER PUBLICATIONS

First Office Action issued in related Chinese Patent Application No. 201180035202.4, dated Jun. 26, 2014, 27 pages.

Search Report issued in related Chinese Patent Application No. 201180035202.4, dated Jun. 18, 2014, 3 pages.

International Search Report issued in International Application No. PCT/US2011/044385, mailed Dec. 6, 2011.

Written Opinion issued in International Application No. PCT/US2011/044385, mailed Dec. 6, 2011.

Notification of Reasons for Refusal issued in related Japanese Patent Application No. 2013-520780, dated Mar. 24, 2015, 8 pages.

* cited by examiner

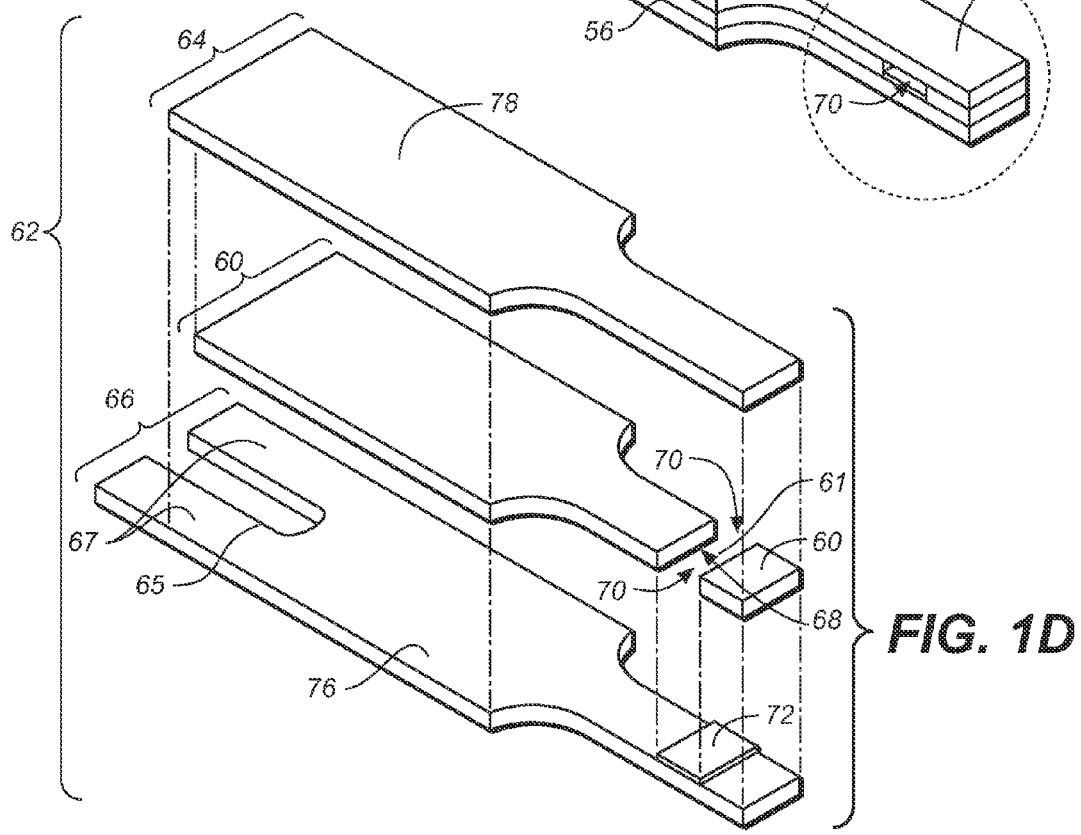
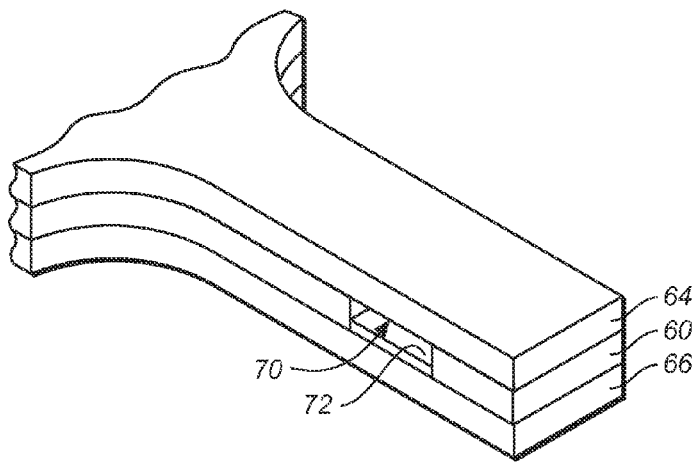

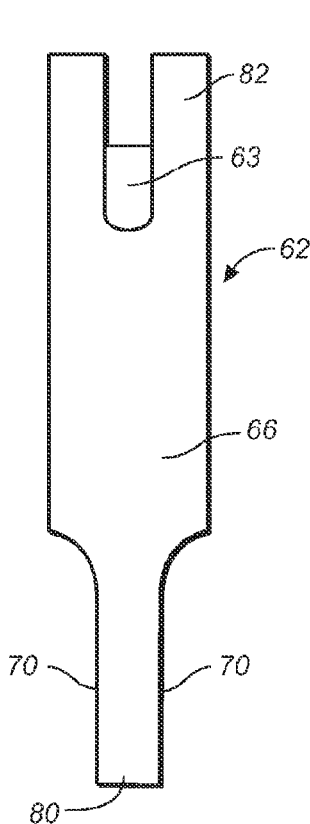 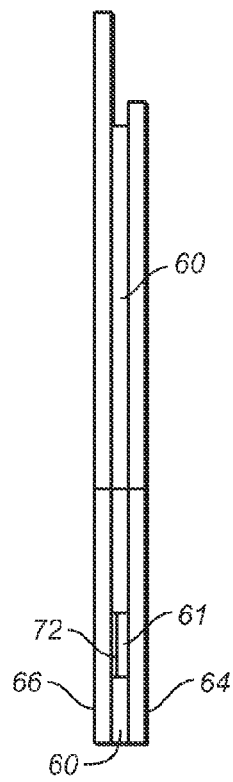 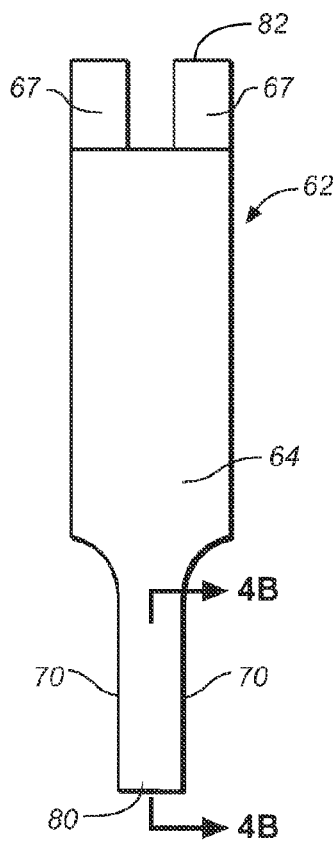
FIG. 2     FIG. 3     FIG. 4A
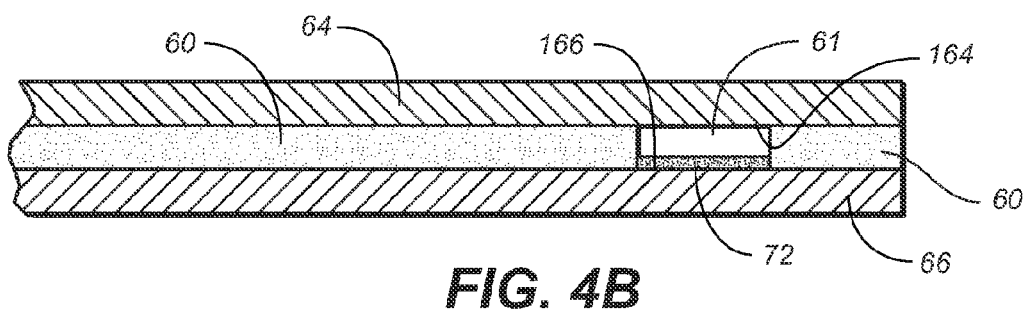
FIG. 4B

SYSTEM AND METHOD FOR MEASURING AN ANALYTE IN A SAMPLE

PRIORITY

This patent application claims the benefits of priority under 35 USC §§119, 120, 365, or 371 from prior patent application Ser. No. 61/365,719; Ser. No. 61/366,099; and 61/442,664, all of the prior applications are incorporated by reference herein to this patent application.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a sample-receiving chamber in an electrochemical cell that includes two electrodes, e.g., a counter and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the initial sample.

Such systems are susceptible to various modes of inefficiency and/or error. For example, variations in temperatures may affect the results of the method. This is especially relevant when the method is carried out in an uncontrolled environment, as is often the case in home applications or in third world countries.

SUMMARY OF THE DISCLOSURE

Applicants have discovered that temperature compensation to a glucose concentration calculation is not necessary when a measured or sampled current is taken at or before a change in a first voltage to a second voltage that are applied to a test trip having two facing electrodes in a test cell with reagent therein.

Various aspects of a method of calculating an analyte concentration of a sample are provided. In one aspect, a method of determining blood glucose concentration with a glucose measurement system is provided. The system includes a test strip and test meter. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; applying a first voltage to between the at least two electrodes of the test strip for a first time interval from the initiation of test sequence to cause a transformation of analytes in the sample; switching the first voltage to a second voltage different than the first voltage; changing the second voltage to a third voltage different from the first or second voltages; measuring a first current output of a current transient from the electrodes during an interval for the switching of the first voltage to the second voltage but prior to a complete changeover to the second voltage; measuring a second current output of the current transient from the electrodes after the changing from the second voltage to the third voltage; estimating a steady state current output of the current transient after the third voltage is maintained at the electrodes; and calculating a blood glucose concentration based on the first, second and third current output of the current transient without compensation for temperature on the glucose concentration.

In another aspect, a method of determining blood glucose concentration with a glucose measurement system is provided. The system includes a test strip and test meter. The test meter has a microcontroller configured to apply a plurality of test voltages to the test strip and measure a current transient output resulting from an electrochemical reaction in a test chamber of the test strip. The method can be achieved by: inserting the test strip into a strip port connector of the test meter to connect at least two electrodes of the test strip to a strip measurement circuit; initiating a test sequence after deposition of a sample; applying a first voltage to between the at least two electrodes of the test strip for a first time interval from the initiation of test sequence to cause a transformation of analytes in the sample; switching the first voltage to a second voltage different than the first voltage; changing the second voltage to a third voltage different from the first or second voltages; measuring a first current output of a current transient from the electrodes during an interval for the switching of the first voltage to the second voltage but prior to a complete changeover to the second voltage; measuring a second current output of the current transient from the electrodes after the changing from the second voltage to the third voltage; estimating a steady state current output of the current transient after the third voltage is maintained at the electrodes; and calculating a blood glucose concentration based on the first, second and third current output of the current transient without compensation for temperature on the glucose concentration with an equation of the form:

$$G_1 = \left(\frac{|i_r|}{|i_l|}\right)^p (a|i_{2CORR}| - zgr);$$

where: $G_1$ comprises a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.0}|}{|i_{4.1}| + b|i_5|}\right) i_r;$$

where a, b, c, p, zgr comprise manufacturing parameters; $i_{4.1}$ is the current measured at about 4.1 seconds after initiation of test sequence; $i_5$ is the current measured at about 5 seconds after initiation of test sequence; $i_{1.0}$ is the current measured at about 1 second after initiation of test sequence.

In a further aspect, a blood glucose measurement system is provided. The system includes an analyte test strip and a meter. The analyte test strip includes a substrate having a reagent disposed thereon and at least two electrodes proximate the reagent in test chamber. The analyte meter includes a strip port connector disposed to connect to the two electrodes, a power supply and a microcontroller electrically coupled to the strip port connector and the power supply so that when the test strip is inserted into the strip port connector and a blood sample is deposited in the test chamber for chemical oxidation or transformations of glucose in the blood sample, a glucose concentration of the blood sample is determined by the microcontroller without additional temperature compensation for the glucose concentration.

In yet another aspect, a glucose measurement system to measure a glucose concentration in physiological fluid of a user is provided. The system includes a test strip having an electrochemical cell with a working electrode, an electrode-electrode and a reagent layer having a mediator in a test area. The electrodes being connectable to corresponding contact pads. The analyte meter includes a microprocessor and a test circuit in connection with a test strip port that electrically connects the contact pads of the test strip so that the meter is configured to apply first, second, and third voltages after deposition of physiological fluid on the electrodes and determine a glucose concentration from a first measured current prior to or at a change in the first voltage to the second voltage, second, third and fourth measured currents, a measured peak current after a change in the second voltage to the third voltage, and a steady state current measured by the meter without any temperature compensation for the glucose concentration.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 1C illustrates a perspective view of an assembled test strip suitable for use in the system and methods disclosed herein;

FIG. 1D illustrates an exploded perspective view of an unassembled test strip suitable for use in the system and methods disclosed herein;

FIG. 1E illustrates an expanded perspective view of a proximal portion of the test strip suitable for use in the system and methods disclosed herein;

FIG. 2 is a bottom plan view of one embodiment of a test strip disclosed herein;

FIG. 3 is a side plan view of the test strip of FIG. 2;

FIG. 4A is a top plan view of the test strip of FIG. 3;

FIG. 4B is a partial side view of a proximal portion of the test strip of FIG. 4A;

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1A:
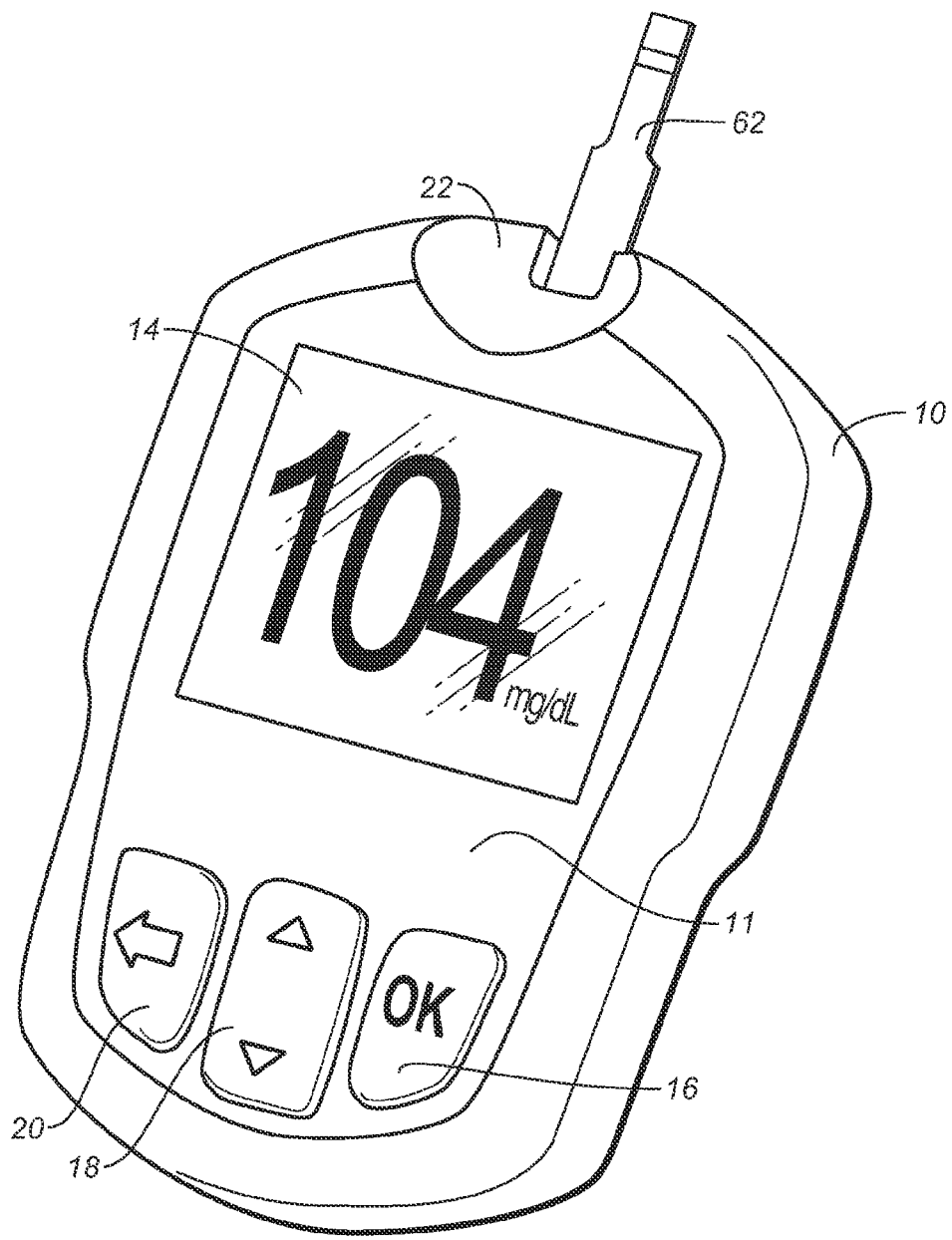
FIG. 1A illustrates a preferred blood glucose measurement system.

FIG. 1A illustrates a diabetes management system that includes a meter 10 and a biosensor in the form of a glucose test strip 62. Note that the meter (meter unit) may be referred to as an analyte measurement and management unit, a glucose meter, a meter, and an analyte measurement device. In an embodiment, the meter unit may be combined with an insulin delivery device, an additional analyte testing device, and a drug delivery device. The meter unit may be connected to a remote computer or remote server via a cable or a suitable wireless technology such as, for example, GSM, CDMA, BlueTooth, WiFi and the like.

Referring back to FIG. 1A, glucose meter or meter unit 10 may include a housing 11, user interface buttons (16, 18, and 20), a display 14, and a strip port opening 22. User interface buttons (16, 18, and 20) may be configured to allow the entry of data, navigation of menus, and execution of commands. User interface button 18 may be in the form of a two way toggle switch. Data may include values representative of analyte concentration, and/or information, which are related to the everyday lifestyle of an individual. Information, which is related to the everyday lifestyle, may include food intake, medication use, occurrence of health check-ups, and general health condition and exercise levels of an individual. The electronic components of meter 10 may be disposed on a circuit board 34 that is within housing 11.

Figure 1B:
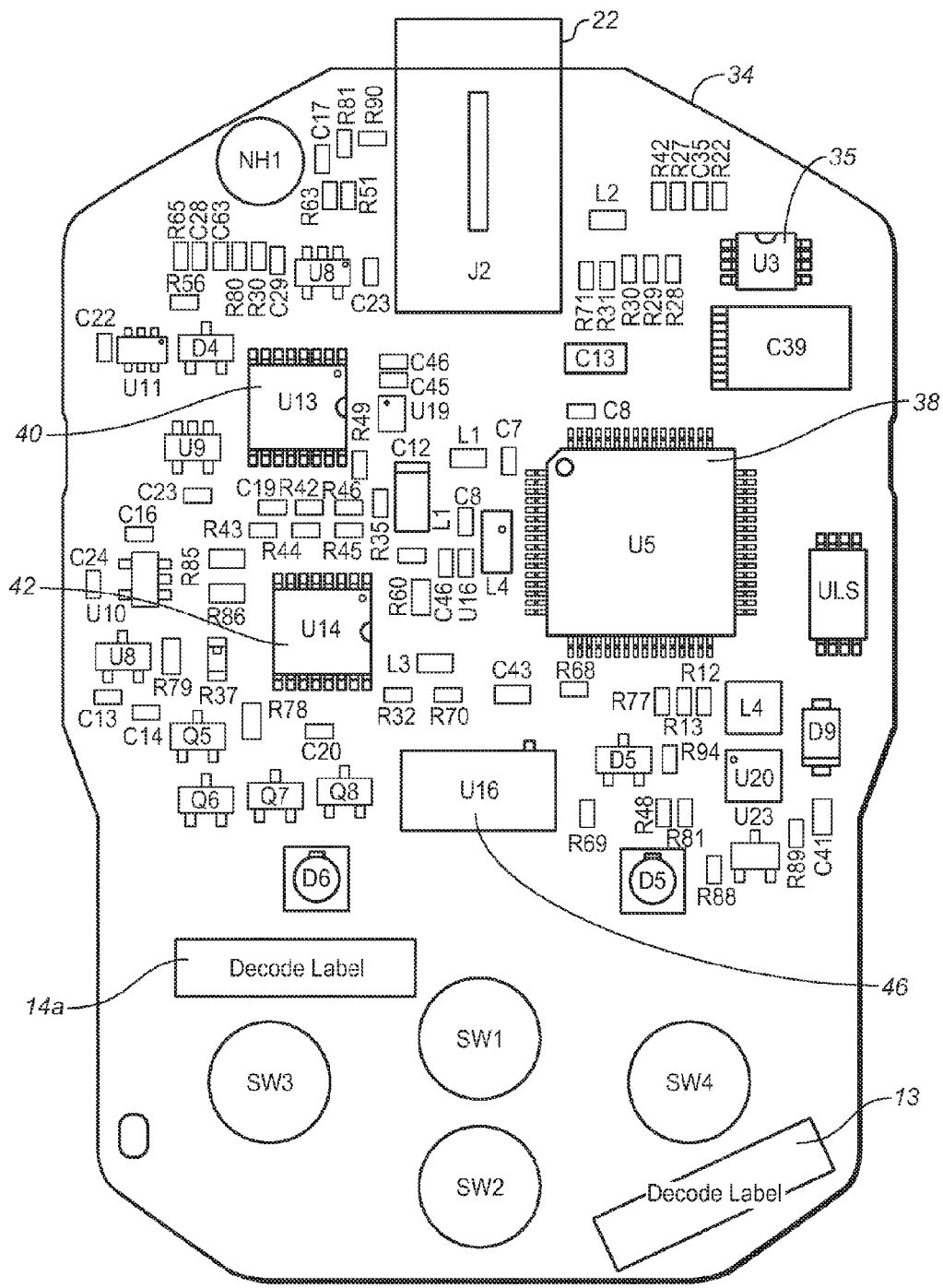
FIG. 1B illustrates the various components disposed in the meter of FIG. 1A.

FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 may be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. Microcontroller 38 may be in the form of a mixed signal microprocessor (MSP) such as, for example, the Texas Instrument MSP 430. The TI-MSP 430 may be configured to also perform a portion of the potentiostat function and the current measurement function. In addition, the MSP 430 may also include volatile and non-volatile memory. In another embodiment, many of the electronic components may be integrated with the microcontroller in the form of an application specific integrated circuit (ASIC).

Strip port connector 22 may be configured to form an electrical connection to the test strip. Display connector 14a may be configured to attach to display 14. Display 14 may be in the form of a liquid crystal display for reporting measured glucose levels, and for facilitating entry of lifestyle related information. Display 14 may optionally include a backlight. Data port 13 may accept a suitable connector attached to a connecting lead, thereby allowing glucose meter 10 to be linked to an external device such as a personal computer. Data port 13 may be any port that allows for transmission of data such as, for example, a serial, USB, or a parallel port. Clock 42 may be configured to keep current time related to the geographic region in which the user is located and also for measuring time. The meter unit may be configured to be electrically connected to a power supply such as, for example, a battery.

FIGS. 1C-1E, 2, 3, and 4B show various views of an exemplary test strip 62 suitable for use with the methods and systems described herein. In an exemplary embodiment, a test strip 62 is provided which includes an elongate body extending from a distal end 80 to a proximal end 82, and having lateral edges 56, 58, as illustrated in FIG. 1C. As shown in FIG. 1D, the test strip 62 also includes a first electrode layer 66, a second electrode layer 64, and a spacer 60 sandwiched in between the two electrode layers 64 and 66. The first electrode layer 66 may include a first electrode 66, a first connection track 76, and a first contact pad 67, where the first connection track 76 electrically connects the first electrode 66 to the first contact pad 67, as shown in FIGS. 1D and 4B. Note that the first electrode 66 is a portion of the first electrode layer 66 that is immediately underneath the reagent layer 72, as indicated by FIGS. 1D and 4B. Similarly, the second electrode layer 64 may include a second electrode 64, a second connection track 78, and a second contact pad 63, where the second connection track 78 electrically connects the second electrode 64 with the second contact pad 63, as shown in FIGS. 1D, 2, and 4B. Note that the second electrode 64 is a portion of the second electrode layer 64 that is above the reagent layer 72, as indicated by FIG. 4B. As used herein, the terms "electrode layer" and "electrode" are used interchangeably to refer to the general area encompassing an electrode or a specific location for the electrode.

As shown, the sample-receiving chamber 61 is defined by the first electrode 66, the second electrode 64, and the spacer 60 near the distal end 80 of the test strip 62, as shown in FIGS. 1D and 4B. The first electrode 66 and the second electrode 64 may define the bottom and the top of sample-receiving chamber 61, respectively, as illustrated in FIG. 4B. A cutout area 68 of the spacer 60 may define the sidewalls of the sample-receiving chamber 61, as illustrated in FIG. 4B. In one aspect, the sample-receiving chamber 61 may include ports 70 that provide a sample inlet and/or a vent, as shown in FIGS. 1C to 1E. For example, one of the ports may allow a fluid sample to ingress and the other port may allow air to egress.

In an exemplary embodiment, the sample-receiving chamber 61 (or test cell or test chamber) may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 cm$^2$ to about 0.2 cm$^2$, about 0.02 cm$^2$ to about 0.15 cm$^2$, or, preferably, about 0.03 cm$^2$ to about 0.08 cm$^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at first electrode 66, may diffuse to second electrode 64 to become reduced, and subsequently diffuse back to first electrode 66 to become oxidized again. Those skilled in the art will appreciate that various such volumes, areas, and/or spacing of electrodes is within the spirit and scope of the present disclosure.

In one embodiment, the first electrode layer 66 and the second electrode layer 64 may be a conductive material formed from materials such as gold, palladium, carbon, silver, platinum, tin oxide, iridium, indium, or combinations thereof (e.g., indium doped tin oxide). In addition, the electrodes may be formed by disposing a conductive material onto an insulating sheet (not shown) by a sputtering, electroless plating, or a screen-printing process. In one exemplary embodiment, the first electrode layer 66 and the second electrode layer 64 may be made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof. In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, and/or the spacer 60 are within the spirit and scope of the present disclosure.

Either the first electrode 66 or the second electrode 64 may perform the function of a working electrode depending on the magnitude and/or polarity of the applied test voltage. The working electrode may measure a limiting test current that is proportional to the reduced mediator concentration. For example, if the current limiting species is a reduced mediator (e.g., ferrocyanide), then it may be oxidized at the first electrode 66 as long as the test voltage is sufficiently greater than the redox mediator potential with respect to the second electrode 64. In such a situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all reduced mediator has been depleted at the working electrode surface such that the measured oxidation current is proportional to the flux of reduced mediator diffusing from the bulk solution towards the working electrode surface. The term "bulk solution" refers to a portion of the solution sufficiently far away from the working electrode where the reduced mediator is not located within a depletion zone. It should be noted that unless otherwise stated for test strip 62, all potentials applied by test meter 10 will hereinafter be stated with respect to second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into a sample-receiving chamber 61 via a port 70. In one aspect, the port 70 and/or the sample-receiving chamber 61 may be configured such that capillary action causes the fluid sample to fill the sample-receiving chamber 61. The first electrode 66 and/or second electrode 64 may be coated with a hydrophilic reagent to promote the capillarity of the sample-receiving chamber 61. For example, thiol derivatized reagents having a hydrophilic moiety such as 2-mercaptoethane sulfonic acid may be coated onto the first electrode and/or the second electrode.

In the analysis of strip 62 above, reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by $GDH_{(ox)}$ and in the process converts $GDH_{(ox)}$ to $GDH_{(red)}$, as shown in the chemical transformation T.1 below. Note that $GDH_{(ox)}$ refers to the oxidized state of GDH, and $GDH_{(red)}$ refers to the reduced state of GDH.

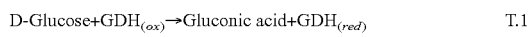

$$D\text{-}Glucose + GDH_{(ox)} \rightarrow Gluconic\ acid + GDH_{(red)} \qquad T.1$$

Next, $GDH_{(red)}$ is regenerated back to its active oxidized state by ferricyanide (i.e. oxidized mediator or $Fe(CN)_6^{3-}$) as shown in chemical transformation T.2 below. In the process of regenerating $GDH_{(ox)}$, ferrocyanide (i.e. reduced mediator or $Fe(CN)_6^{4-}$) is generated from the reaction as shown in T.2:

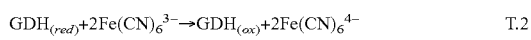

$$GDH_{(red)} + 2Fe(CN)_6^{3-} \rightarrow GDH_{(ox)} + 2Fe(CN)_6^{4-} \qquad T.2$$

Figure 5:
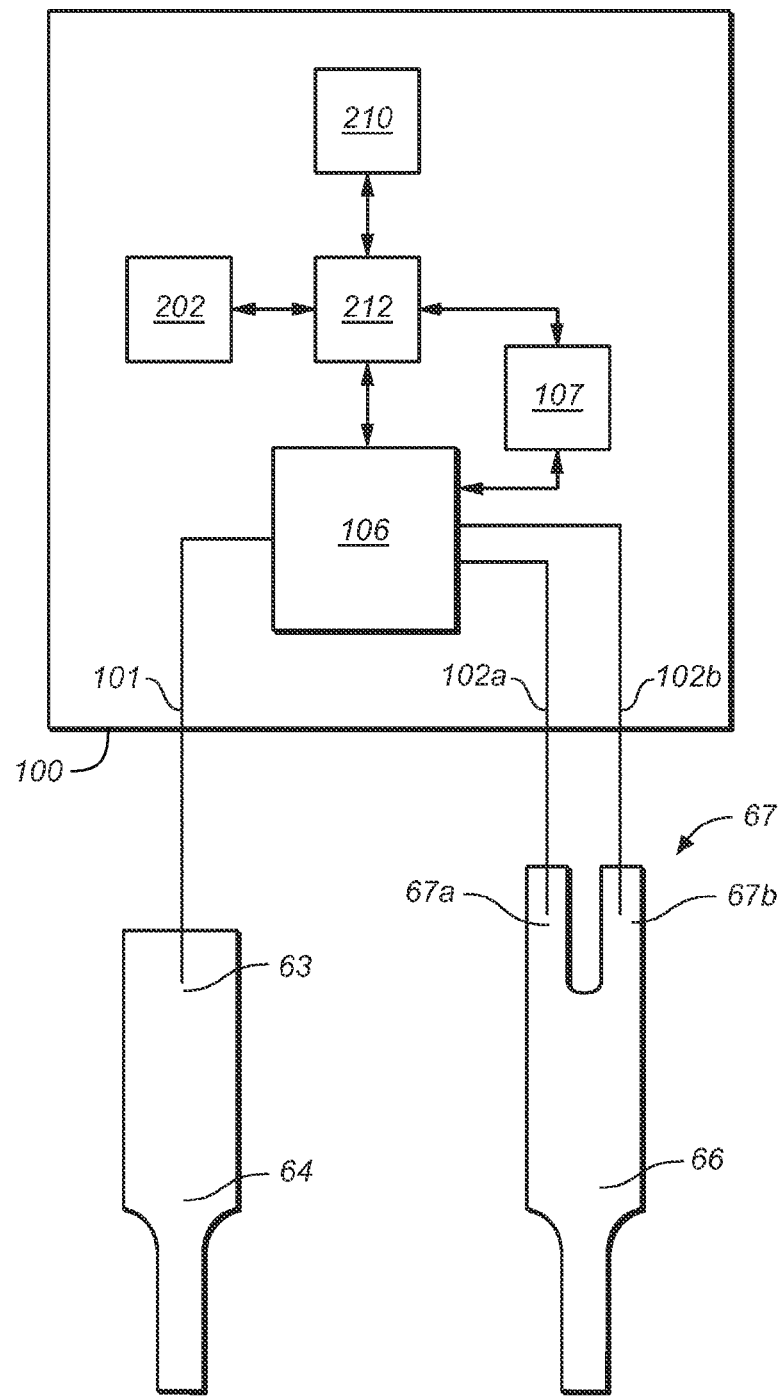
FIG. 5 is a simplified schematic showing a test meter electrically interfacing with portions of a test strip disclosed herein.

FIG. 5 provides a simplified schematic showing a test meter 100 interfacing with a first contact pad 67a, 67b and a second contact pad 63. The second contact pad 63 may be used to establish an electrical connection to the test meter through a U-shaped notch 65, as illustrated in FIG. 2. In one embodiment, the test meter 100 may include a second electrode connector 101, and a first electrode connectors (102a, 102b), a test voltage unit 106, a current measurement unit 107, a processor 212, a memory unit 210, and a visual display 202, as shown in FIG. 5. The first contact pad 67 may include two prongs denoted as 67a and 67b. In one exemplary embodiment, the first electrode connectors 102a and 102b separately connect to prongs 67a and 67b, respectively. The second electrode connector 101 may connect to second contact pad 63. The test meter 100 may measure the resistance or electrical continuity between the prongs 67a and 67b to determine whether the test strip 62 is electrically connected to the test meter 10.

In one embodiment, the test meter 100 may apply a test voltage and/or a current between the first contact pad 67 and the second contact pad 63. Once the test meter 100 recognizes that the strip 62 has been inserted, the test meter 100 turns on and initiates a fluid detection mode. In one embodiment, the fluid detection mode causes test meter 100 to apply a constant current of about 1 microampere between the first electrode 66 and the second electrode 64. Because the test strip 62 is initially dry, the test meter 10 measures a relatively large voltage. When the fluid sample bridges the gap between the first electrode 66 and the second electrode 64 during the dosing process, the test meter 100 will measure a decrease in measured voltage that is below a predetermined threshold causing test meter 10 to automatically initiate the glucose test.

Figure 6A:
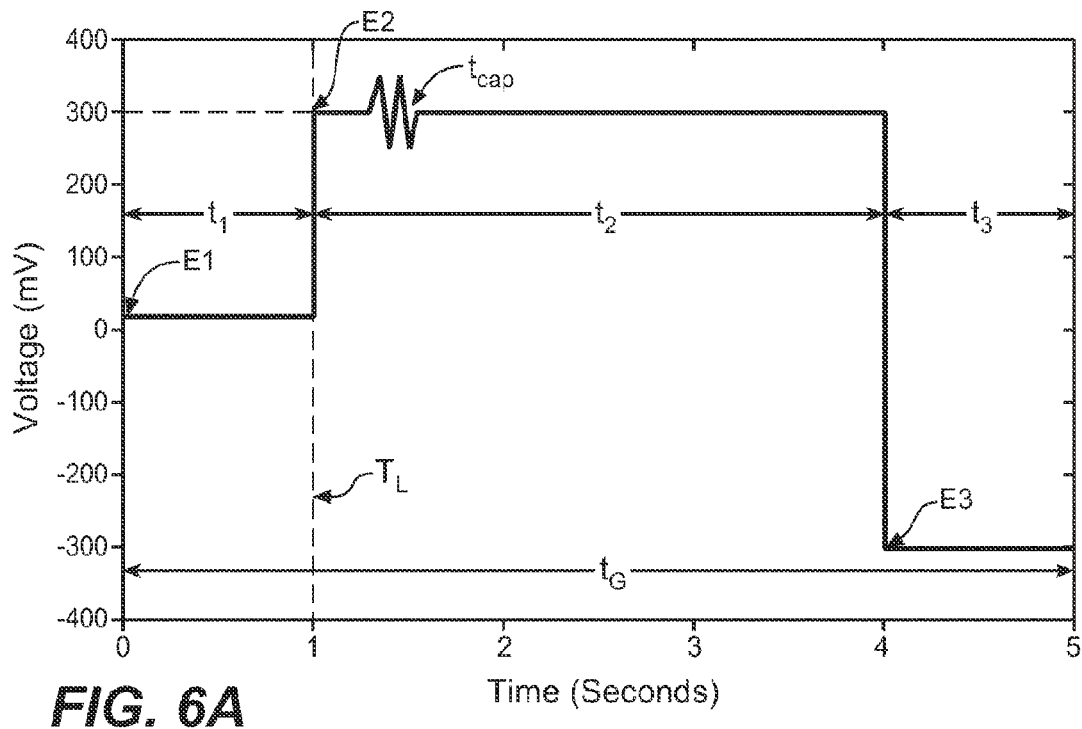
FIG. 6A shows an example of a tri-pulse potential waveform applied by the test meter of FIG. 5 to the working and counter electrodes for prescribed time intervals.

In one embodiment, the test meter 100 may perform a glucose test by applying a plurality of test voltages for prescribed intervals, as shown in FIG. 6A. The plurality of test voltages may include a first test voltage E1 for a first time interval $t_1$, a second test voltage E2 for a second time interval $t_2$, and a third test voltage E3 for a third time interval $t_3$. The third voltage E3 may be different in the magnitude of the electromotive force, in polarity, or combinations of both with respect to the second test voltage E2. In the preferred embodiments, E3 may be of the same magnitude as E2 but opposite in polarity. A glucose test time interval $t_G$ represents an amount of time to perform the glucose test (but not necessarily all the calculations associated with the glucose test). Glucose test time interval $t_G$ may range from about 1 second to about 5 seconds. Further, as illustrated in FIG. 6A, the second test voltage E2 may include a constant (DC) test voltage component and a superimposed alternating (AC), or alternatively oscillating, test voltage component. The superimposed alternating or oscillating test voltage component may be applied for a time interval indicated by $t_{cap}$.

The plurality of test current values measured during any of the time intervals may be performed at a frequency ranging from about 1 measurement per microsecond to about one measurement per 100 milliseconds. While an embodiment using three test voltages in a serial manner is described, the glucose test may include different numbers of open-circuit and test voltages. For example, as an alternative embodiment, the glucose test could include an open-circuit for a first time interval, a second test voltage for a second time interval, and a third test voltage for a third time interval. It should be noted that the reference to "first," "second," and "third" are chosen for convenience and do not necessarily reflect the order in which the test voltages are applied. For instance, an embodiment may have a potential waveform where the third test voltage may be applied before the application of the first and second test voltage.

Once the glucose assay has been initiated, the test meter 10 may apply a first test voltage E1 (e.g., approximately 20 mV in FIG. 6A) for a first time interval $t_1$ (e.g., 1 second in FIG. 6A). The first time interval $t_1$ may range from about 0.1 seconds to about 3 seconds and preferably range from about 0.2 seconds to about 2 seconds, and most preferably range from about 0.3 seconds to about 1 second.

Figure 6B:
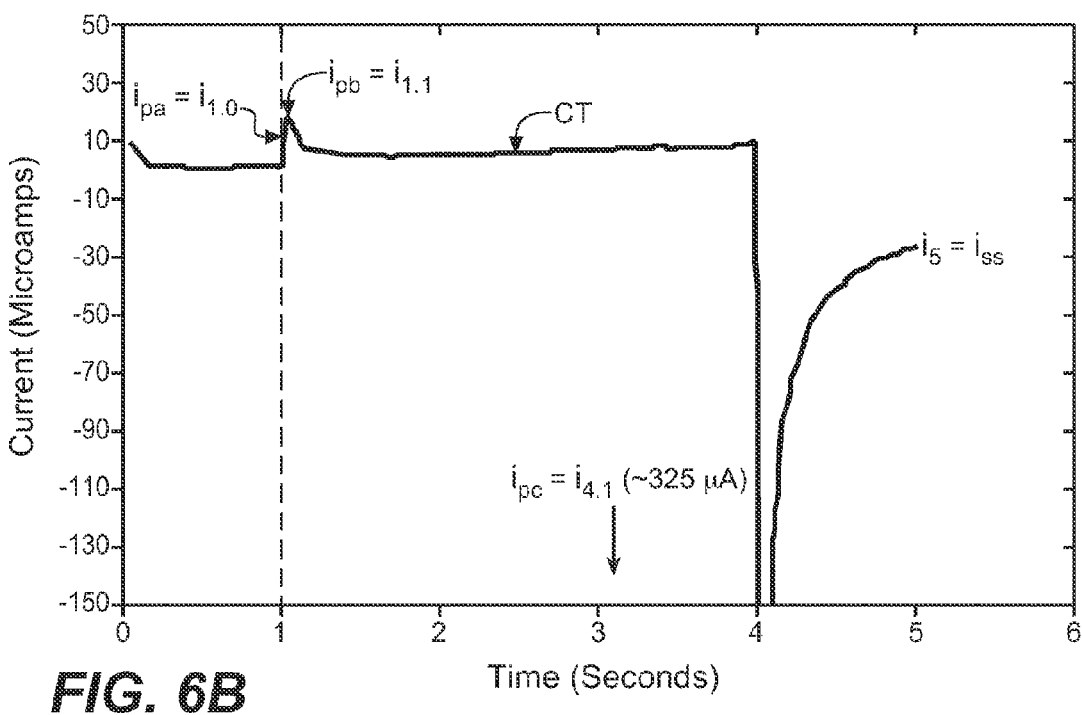
FIG. 6B shows a current transient CT generated testing a physiological sample.

The first time interval $t_1$ may be sufficiently long so that the sample-receiving chamber 61 may fully fill with sample and also so that the reagent layer 72 may at least partially dissolve or solvate. In one aspect, the first test voltage E1 may be a value relatively close to the redox potential of the mediator so that a relatively small amount of a reduction or oxidation current is measured. FIG. 6B shows that a relatively small amount of current is observed during the first time interval $t_1$ compared to the second and third time intervals $t_2$ and $t_3$. For example, when using ferricyanide and/or ferrocyanide as the mediator, the first test voltage E1 in FIG. 6A may range from about 1 mV to about 100 mV, preferably range from about 5 mV to about 50 mV, and most preferably range from about 10 mV to about 30 mV. Although the applied voltages are given as positive values in the preferred embodiments, the same voltages in the negative domain could also be utilized to accomplish the intended purpose of the claimed invention.

After applying the first test voltage E1, the test meter 10 applies a second test voltage E2 between first electrode 66 and second electrode 64 (e.g., approximately 300 mVolts in FIG. 6A), for a second time interval $t_2$ (e.g., about 3 seconds in FIG. 6A). The second test voltage E2 may be a value sufficiently negative of the mediator redox potential so that a limiting oxidation current is measured at the second electrode 64. For example, when using ferricyanide and/or ferrocyanide as the mediator, the second test voltage E2 may range from about zero mV to about 600 mV, preferably range from about 100 mV to about 600 mV, and more preferably is about 300 mV.

The second time interval $t_2$ should be sufficiently long so that the rate of generation of reduced mediator (e.g., ferrocyanide) may be monitored based on the magnitude of a limiting oxidation current. Reduced mediator is generated by enzymatic reactions with the reagent layer 72. During the second time interval $t_2$, a limiting amount of reduced mediator is oxidized at second electrode 64 and a non-limiting amount of oxidized mediator is reduced at first electrode 66 to form a concentration gradient between first electrode 66 and second electrode 64.

In an exemplary embodiment, the second time interval $t_2$ should also be sufficiently long so that a sufficient amount of ferricyanide may be generated or diffused at the second electrode 64. A sufficient amount of ferricyanide is required at the second electrode 64 so that a limiting current may be measured for oxidizing ferrocyanide at the first electrode 66 during the third test voltage E3. The second time interval $t_2$ may be less than about 60 seconds, and preferably may range from about 1 second to about 10 seconds, and more preferably range from about 2 seconds to about 5 seconds. Likewise, the time interval indicated as $t_{cap}$ in FIG. 6A may also last over a range of times, but in one exemplary embodiment it has a duration of about 20 milliseconds. In one exemplary embodiment, the superimposed alternating test voltage component is applied after about 0.3 seconds to about 0.4 seconds after the application of the second test voltage E2, and induces a sine wave having a frequency of about 109 Hz with an amplitude of about +/−50 mV.

FIG. 6B shows a relatively small peak $i_{pb}$ after the beginning of the second time interval $t_2$ followed by a gradual increase of an absolute value of an oxidation current during the second time interval $t_2$. The small peak $i_{pb}$ occurs due to an initial depletion of reduced mediator after a transition from first voltage E1 to second voltage E2, referenced here as transition line $T_L$. Thereafter, there is a gradual absolute decrease in oxidation current after the small peak $i_{pb}$ is caused by the generation of ferrocyanide by reagent layer 72, which then diffuses to second electrode 64.

After applying the second test voltage E2, the test meter 10 applies a third test voltage E3 between the first electrode 66 and the second electrode 64 (e.g., about −300 mVolts in FIG. 6A) for a third time interval $t_3$ (e.g., 1 second in FIG. 6A). The third test voltage E3 may be a value sufficiently positive of the mediator redox potential so that a limiting oxidation current is measured at the first electrode 66. For example, when using ferricyanide and/or ferrocyanide as the mediator, the third test voltage E3 may range from about zero mV to about −600 mV, preferably range from about −100 mV to about −600 mV, and more preferably is about −300 mV.

The third time interval $t_3$ may be sufficiently long to monitor the diffusion of reduced mediator (e.g., ferrocyanide) near the first electrode 66 based on the magnitude of the oxidation current. During the third time interval $t_3$, a limiting amount of reduced mediator is oxidized at first electrode 66 and a non-limiting amount of oxidized mediator is reduced at the second electrode 64. The third time interval $t_3$ may range from about 0.1 seconds to about 5 seconds and preferably range from about 0.3 seconds to about 3 seconds, and more preferably range from about 0.5 seconds to about 2 seconds.

FIG. 6B shows a relatively large peak $i_{pc}$ at the beginning of the third time interval $t_3$ followed by a decrease to a steady-state current $i_{ss}$ value. In one embodiment, the second test voltage E2 may have a first polarity and the third test voltage E3 may have a second polarity that is opposite to the first polarity. In another embodiment, the second test voltage E2 may be sufficiently negative of the mediator redox potential and the third test voltage E3 may be sufficiently positive of the mediator redox potential. The third test voltage E3 may be applied immediately after the second test voltage E2. However, one skilled in the art will appreciate that the magnitude and polarity of the second and third test voltages may be chosen depending on the manner in which analyte concentration is determined.

A blood glucose concentration can be determined based on the test current values. A first glucose concentration $G_1$ may be calculated using a glucose algorithm as shown in Equation 1:

$$G_1 = \left(\frac{i_2}{i_3}\right)^p \times (a \times i_1 - z) \qquad \text{Eq. 1}$$

Where $i_1$ is a first test current value,
$i_2$ is a second test current value,
$i_3$ is a third test current value, and
the terms a, p, and z can be empirically derived calibration constants.

All test current values (e.g., $i_1$, $i_2$, and $i_3$) in Equation 1 use the absolute value of the current. The first test current value $i_1$ and the second test current value $i_2$ can each be defined by an average or summation of one or more predetermined test current values that occur during the third time interval $t_3$. The term $i_2$ is a second current value that is based on a fourth current value $i_4$, a fifth current value $i_5$, and a sixth current value $i_6$, which are all measured during a third time interval. The third test current value $i_3$ can be defined by an average or summation of one or more predetermined test current values that occur during the second time interval $t_2$. One skilled in the art will appreciate that names "first," "second," and "third" are chosen for convenience and do not necessarily reflect the order in which the current values are calculated. A derivation of Eq. 1 can be found in U.S. Pat. No. 7,749,371, patented Jul. 6, 2010, which was filed on 30 September, 2005 and entitled "Method and Apparatus for Rapid Electrochemical Analysis," which is hereby incorporated by reference in its entirety into this application.

Referring now to FIGS. 6A and 6B, the peak current (FIG. 6B) observed after the start (i.e., transition line $T_L$) of the second test potential time interval $t_2$ (FIG. 6A) may be denoted as $i_{pb}$, and the peak current exhibited at the start of the third test potential time interval $t_3$ (FIG. 6A) may be denoted as $i_{pc}$. Equation 2 describes a relationship between the first current transient CT and second current transient CT when a test strip 62 is tested with a sample containing an interferent and no glucose.

$$i_{pc} - 2i_{pb} = -i_{ss} \qquad \text{Eq. 2}$$

Because there is typically no glucose in the sample during the first time period $t_1$, it is believed that the reagent layer 72 does not generate substantial amount of reduced mediator. Therefore, the current transients would reflect only the oxidation of interferents. At the early time scale regime of around 1.0 seconds, it is assumed that reagent layer 72 does not generate a significant amount of reduced mediator because of the glucose reaction. Further, it is assumed that the reduced mediator which is generated will mostly remain near first electrode 66, where reagent layer 72 was initially deposited, and not significantly diffuse to second electrode 64. Therefore, the magnitude of $i_{pb}$ is predominantly ascribed to interferent oxidation at second electrode 64 which is a direct interferent current.

At a duration after the third voltage E3 has been provided to the strip (e.g., about −300 mV) at around 4.1 seconds, reagent layer 72 does generate a significant amount of reduced mediator at first electrode 66 in the presence of glucose because of the glucose reaction. A significant amount of reduced mediator can also be generated because of a possible oxidation of an interferent with the oxidized mediator. As mentioned earlier, interferent that reduces oxidized mediator contributes to a current which may be referred to as an indirect current. In addition, interferents can also be oxidized directly at first electrode 66 which may be referred to as a direct current. For the situation in which the mediator can be oxidized at the working electrode, it may be assumed that the sum of the direct oxidation and indirect oxidation is approximately equal to a direct oxidation current that would have been measured if there was no oxidized mediator disposed on the working electrode. In summary, the magnitude of the $i_{pb}$ is ascribed to both indirect and direct interferent oxidation, and the glucose reaction at one of the first electrode 66 or second electrode 64. Because it has been determined that $i_{pb}$ is controlled mainly by interferents, $i_{pc}$ can be used with $i_{pb}$ together to determine a correction factor. For example, as shown below $i_{pb}$ can be used with $i_{pc}$ in a mathematical function to determine a corrected current $i_{2(Corr)}$ which is proportional to glucose and less sensitive to interferents:

$$i_{2(CORR)} = i_2 \left[ \frac{i_{pc} - 2i_{pb} + i_{ss}}{i_{pc} + i_{ss}} \right] \qquad \text{Eq. 3}$$

Eq. 3 was empirically derived to calculate a current $i_{2(Corr)}$ which is proportional to glucose and has a relative fraction of current removed that is ascribed to interferents. The term $i_{ss}$ was added to both the numerator and denominator to allow the numerator to approach zero when no glucose is present. Determination of the steady-state current $i_{ss}$ following application of the second electric potential is detailed in co-pending patent application Ser. No. 11/278,341, which is incorporated by reference into this application herein. Some examples of methods for calculating $i_{ss}$ can be found in U.S. Pat. Nos. 5,942,102 and 6,413,410, each of which is hereby incorporated by reference in its entirety.

Referring back now to Equation 1, Equation 3 can be represented in terms of $i_1$, $i_3$ and $i_2$ as based on current measurements $i_4$, $i_5$, $i_6$, and $i_7$ as Equation 4:

$$i_2 = i_4 \left\{ \frac{i_5 - Fi_7 + bi_6}{i_5 + bi_6} \right\} \qquad \text{Eq. 4}$$

Where, as before, $i_2$ is a second current value that is based on a fourth current value $i_4$, a fifth current value $i_5$, and a sixth current value $i_6$ which are all measured during a third time interval $t_3$, and $i_7$ which in one embodiment is a seventh current value measured in a first time interval $t_1$, and b and F are empirically derived constants. The time window for each current measurement is discussed below.

This technique of accounting for the presence of interferents in an analyte can now be further refined to account for effects due to variation in temperature. In one example embodiment, $i_7$ may be the test current value measured at an interval during a ramping from the first voltage E1 to the second voltage, which for convenience, has been designated as approximately 1.0 seconds into the test. While this ramped current $i_7$ has been observed as a current change in an interval from the ramping of the first voltage E1 to the second voltage E2 at the transition line $T_L$, ramped current $i_7$ may be measured at a time point within a suitable range as defined by a current measured when the first voltage E1 is in the process of ramping to the second voltage E2 (from 0.7 second to near 1.1 second in FIG. 6B) but not the current measured once the first voltage E1 has been switched over completely to the second voltage E2, (after transition line $T_1$, or about 1.1 or more seconds in FIG. 6B). In the preferred embodiment and for ease of computational processing, applicants have selected ramped current $i_7$ as the test current measured at a test time equal to 1.0 seconds into the current transient caused by the change in voltages from E1 to E2, but it should be clear that the ramped current $i_7$ may vary depending on the particular configurations of the relevant test strip.

Equation 4 can be modified to provide an even more accurate glucose concentration. Instead of using a simple average of summation of test current values, the term $i_1$ can be defined to include peak current values $i_{pb}$ and $i_{pc}$ and the steady-state current $i_{ss}$, as shown in Equation 5, which is similar to Equation 3:

$$i_1 = i_2 \left\{ \frac{i_{pc} - 2i_{pb} + i_{ss}}{i_{pc} + i_{ss}} \right\} \qquad \text{Eq. 5}$$

where a calculation of the steady-state current $i_{ss}$ can be based on a mathematical model, an extrapolation, an average at a predetermined time interval, a combination thereof, or any number of other ways for calculating a steady-state current.

Alternatively, $i_{ss}$ may be estimated by multiplying the test current value at 5 seconds with a constant $K_8$ (e.g., 0.678). Thus, $i_{ss} \approx i(5) \times K_8$. The term $K_8$ can be estimated using Equation 6:

$$iss = \frac{i(5)}{1 + 4\exp\left(\frac{-4\pi^2 Dx 0.975}{L^2}\right)} \quad \text{Eq. 6}$$

where the number 0.975 is about the time in seconds after the third test voltage E3 is applied that corresponds to the current at approximately 5 seconds for the particular embodiment of the strip 62, which, assuming a linear variation over the time between about 0.95 seconds and 1 second, is the average current between 0.95 and 1 second, the term D is assumed to be about $5 \times 10^{-6}$ cm²/sec as a typical diffusion coefficient in blood, and the term L is assumed to be about 0.0095 cm, which represents the height of the spacer 60.

Turning again to Eq. 3, $i_{pc}$ may be the test current value at about 4.1 seconds, and $i_{pb}$ may be the test current value at about 1.1 second, based on the test voltage and test current waveforms in FIGS. 6A and 6B.

Turning back to Eq. 1, $i_2$ may be defined to be $$i_2 = \sum_{t=4.4}^{5} i(t)$$

and $i_3$ may be defined to be $$i_3 = \sum_{t=1.4}^{4} i(t).$$

Equation 3 may be combined with Equations 1 and 2 to yield an equation for determining a more accurate glucose concentration that may compensate for the presence of endogenous and/or exogenous interferents in a blood sample, as shown in Equation 7:

$$G_1 = \left(\frac{i_2}{i_3}\right)^p \times \left(\alpha \times i_2 \times \left\{\frac{i_{pc} - 2i_{pb} + i_{ss}}{i_{pc} + i_{ss}}\right\} - z\right) \quad \text{Eq. 7}$$

where the first glucose concentration $G_1$ is the output of the blood glucose algorithm and the terms a, p, and z are constants that may be derived empirically from manufacturing samples of the test strip.

The selection of the time intervals in which $i_1$, $i_3$ and $i_2$ may be calculated is described in co-pending Patent Application Publication No. 2007/0227912 entitled 'Methods and Apparatus for Analyzing a Sample in the Presence of Interferents', and methods for calibrating strip lots are described in U.S. Pat. No. 6,780,645, both of which are hereby incorporated by reference in their entirety into this application.

In the preferred embodiment, the glucose concentration $G_1$ of Equation 7 is determined by Equation 8 that utilizes current $i_{2(Corr)}$, (which is proportional to glucose and has a relative fraction of current removed that is ascribed to interferents):

$$G_1 = \left(\frac{|i_r i_l|}{|i_l|}\right)^p (a|i_{2CORR}| - zgr); \quad \text{Eq. 8}$$

where:

$$i_r = \sum_{t=4.4}^{t=5} i(t); \quad \text{Eq. 8.1}$$

$$i_l = \sum_{t=1.4}^{t=4} i(t);$$

$$i_{2(Corr)} = \left(\frac{|i_{pc}| + b|i_{ss}| - 2|i_{pb}|}{|i_{pc}| + b|i_{ss}|}\right) i_r;$$

and
a, b, p, and zgr are manufacturing parameters.

In an alternative embodiment shown and described in copending U.S. Patent Publication No. 2009/0301899 (hereafter "the '899 application"), the current $i_{pb}$ was selected to be a current measured when the voltage applied to the electrodes are greater than 20 mV, and approximately 300 mV. Consequently, in the embodiment of the '899 application, the current is measured (in FIG. 6B) when the applied voltage is 300 mV (in FIG. 6A). The system thus looks for a current value for the current output $i_{pb}$ at about 1.1 seconds to ensure that the applied voltage is actually at about 300 mV. In using the current $i_{pb}$ at about 1.1 seconds, applicants have had to compensate for the effect of ambient temperature on the test strip 62. Because temperature compensation must be performed on the glucose value $G_1$, applicants will now designate this embodiment shown and described in the '899 application as a "mandatory-temperature-compensated-glucose-concentration."

In this mandatory-temperature-compensated-glucose-concentration calculation, $i_{pb}$ is the current measured at approximately 1.1 second; $i_{pc}$ is current measured from the electrodes of the strip 62 at approximately 4.1 seconds; $i_{ss}$ is the current measured at approximately 5 seconds. For ease of notation, Eq. 8.1 for this mandatory-temperature-compensated-glucose-concentration calculation, can be represented in the following notation as Equation 8.2:

$$i_{2(Corr)} = \left(\frac{|i_{4.1}| + b|i_5| - 2|i_{1.1}|}{|i_{4.1}| + b|i_5|}\right) i_r \quad \text{Eq. 8.2}$$

It has been discovered by applicants that if the current $i_{pb}$ is measured when the applied voltage to the strip (FIG. 6A) is less than 300 mV (and preferably less than 100 mV, and most preferably about 20 mV) then the effect of ambient temperature is reduced significantly on the glucose reaction. Of particular surprise to applicants was the discovery that after a duration at which the applied voltage is about 20 mV and prior to the driving voltage being stepped up to 300 mV, the measured current in this interval (indicated at $i_{pa}$ instead of at $i_{pb}$ in FIG. 6B) allows for determination of glucose concentration without any need for temperature compensation due to the ambient temperature affecting the electrochemical reaction occurring on the strip 62.

Consequently, in a preferred embodiment of this application, the measured current in this interval is selected to be the measured current at any time at or prior to the transition from low voltage (e.g., 20 mV) to the higher voltage (e.g., 300 mV) indicated line $T_L$. Due to the imprecise nature of determining where the transition line $T_L$ (at which the low voltage E1 is changed over to the higher voltage E2 in FIG. 6A) is reflected on the current transient CT of FIG. 6B, applicants have elected to measure the current transient at 1 second. Hence, in Equation 8.1, $i_{pc}$ and $i_{ss}$ have the same value as in Eq. 8.3 but measured current in time period $t_2$ is the current measured at approximately 1 second (or at any time at or prior to the transition line $T_L$ while the applied voltage remains less than 300 mV). This measured current is designated here as $i_{pa}$ in Equation 8.3, with a scaling factor "c" so that no changes need be made to the other manufacturing parameter b.

$$i_{2(Corr)} = \left( \frac{|i_{pc}| + b|i_{ss}| - c|i_{pa}|}{|i_{pc}| + b|i_{ss}|} \right) i_r \qquad \text{Eq. 8.3}$$

Because manufacturing parameter b remains generally consistent in the manufacturing process, once such parameter b has been determined, the scaling factor c in Eq. 8.3 may be from about 5 to about 25 (preferably about 20) to allow the parameter b to remain the same as was previously determined in the manufacturing process.

For ease of notation, Eq. 8.3, as applied to the present embodiment, can be represented in the following notation as Eq. 8.4:

$$i_{2(Corr)} = \left( \frac{|i_{4.1}| + b|i_5| - c|i_{1.0}|}{|i_{4.1}| + b|i_5|} \right) i_r \qquad \text{Eq. 8.4}$$

The measurement of the test current at or prior to transition line $T_L$ (or for ease of calculation, at 1.0 second) in Eq. 8.3 provides a value of the test current which is believed to be more sensitive to temperature variations. In other words, it is believed that the glucose concentration is inherently correct without further compensation using a specific algorithm as provided for in the '899 application when the measured or sampled current $i_{pb}$ is taken at or prior to transition line $T_L$ during which the applied voltage is less than 300 mV and preferably about 20 mV. The surprising benefit of measuring the output current $i_{pa}$ prior to a complete changeover to the second voltage E2 will now be demonstrated in relation to FIGS. 7A-7E.

Figure 7A:
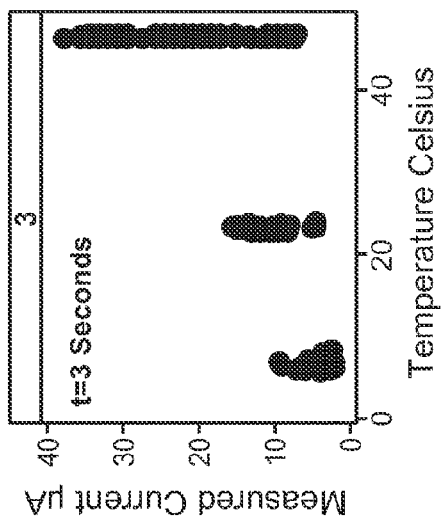
FIGS. 7A, 7B, 7C, 7D, and 7E illustrate test current, measured at increasing time into the current transient CT, against temperature to show the correlation between measured current and temperature depending on when the output current is measured on the strip.
Figure 7B:
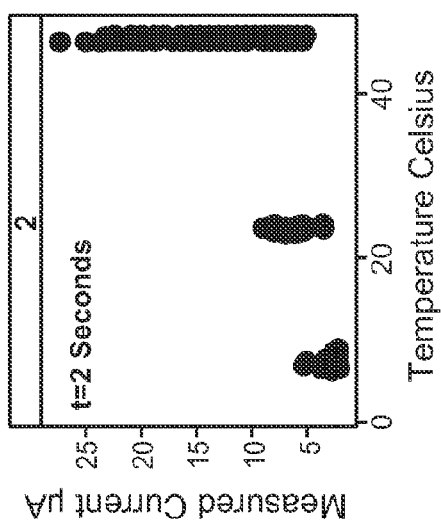
Figure 7C:
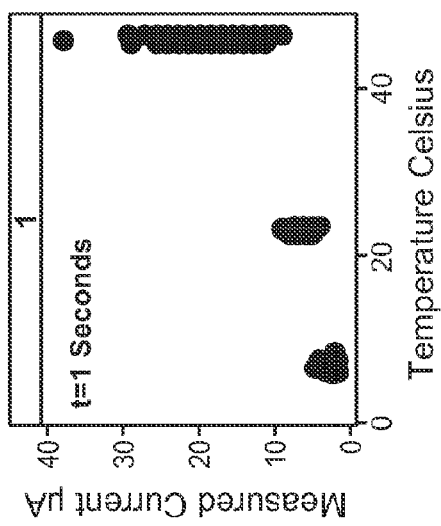
Figure 7D:
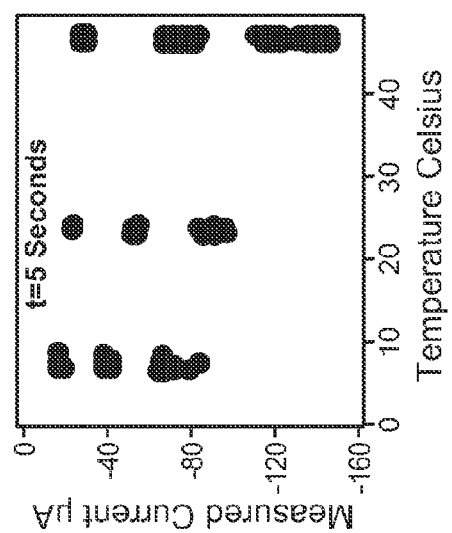
Figure 7E:
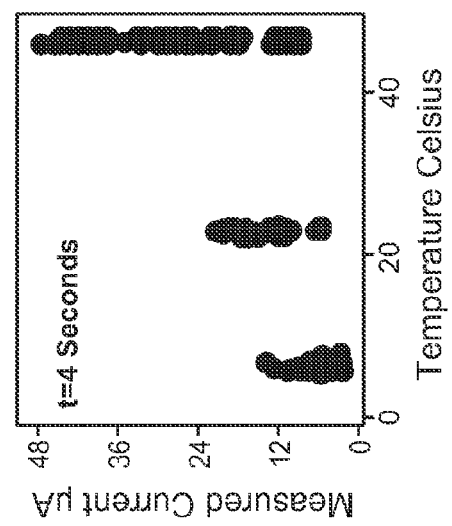

FIGS. 7A, 7B, 7C, 7D, and 7E are five separate plots showing measured test current taken at different time periods during the current transients of FIG. 6B, and how the test current is impacted by temperature. To ensure data sufficiently reflective of actual strip usage, the data of FIGS. 7A-7E include samples having a range of glucose concentrations from 70 mg/dL to greater than 500 mg/dL, with 3 different lots of test strips were used, as well as several blood donors and normal haematocrit level. In FIG. 7A, when the applied voltage of FIG. 6A is approximately 20 mV over a selected ambient temperature range from 0 degree Celsius to 40 degrees Celsius, it can be seen that the measured currents taken vary in FIG. 7A by no more than approximately 8 microamps. As shown in FIG. 7B, when the driving voltage of FIG. 6A is approximately 300 mV over the temperature range, the measured current (taken at about 2 seconds) vary by up to 25 microamps, indicating that there is a correlation in the measured current between temperature and the applied voltage. FIGS. 7C-7E further confirm this correlation. The level of correlation between test current values and temperature is shown to vary with increasing time into the current transient. The measured or sampled current $i_{pa}$ is taken at or prior to transition line $T_L$ (at 1.0 second) into the current transient depicted in FIG. 7A reveals a high correlation with temperature. This temperature dependency, however, is shown in FIGS. 7B to 7E to decline over time and therefore measured or sampled current $i_{pa}$ (instead of $i_{pb}$ in FIG. 6B)

taken at or prior to transition line $T_L$ while the applied voltage is low (less than 300 mV and preferably about 20 mV) is believed to be most suitable to achieving an accurate glucose concentration calculation. Although the applied voltages are given as positive values in the preferred embodiments, the same voltages in the negative domain could also be utilized to accomplish the intended purpose of the invention.

Figure 8:
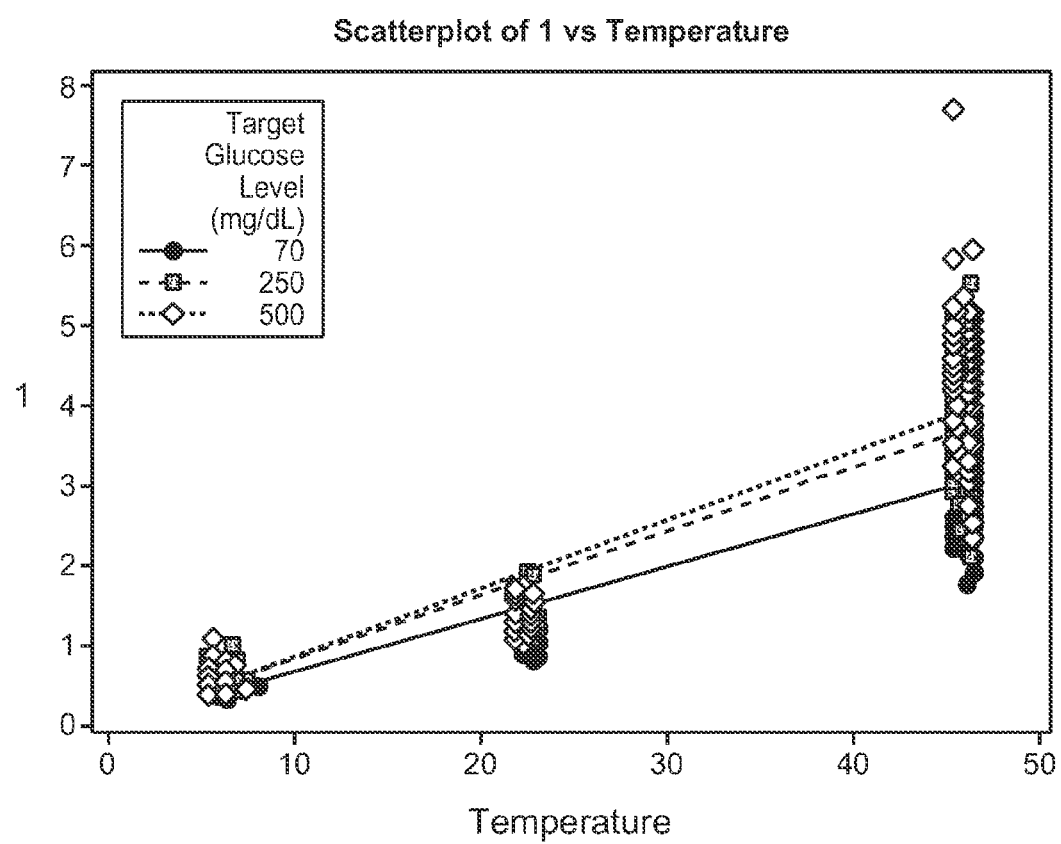
FIG. 8 is a plot of test current values measured at 1 second versus temperature for samples having either a low, medium or high glucose concentration.

FIG. 8 shows a plot of test current values measured in the interval before the change in voltage from 20 mV to 300 mV (at approximately 1.0 second) versus temperature (° C.) for samples having either a low glucose concentration (70 mg/dL), medium glucose concentration (250 mg/dL) or a high glucose concentration (500 mg/dL). Measurement of the three glucose concentrations was carried out at three discrete temperatures, 7° C., 23° C. and 43° C. FIG. 8 shows the data grouped for each temperature based upon their glucose values, and reveals a strong correlation between the measured or sampled current $i_{pa}$ (taken at or prior to transition line $T_L$) and temperature. Furthermore, the measured or sampled test currents during this ramped-up interval are more highly correlated to temperature than they are to glucose concentration. Because the sampled current is highly correlated to temperature, applicants believe that using these current values in the algorithm will reduce the sensitivity of the calculated glucose concentration with temperature, and therefore, no further temperature compensation for the glucose concentration is necessary.

Measurement of current at or prior to transition line $T_L$ while voltage is less than 300 mV into the current transient CT represents the last measurement point within time interval $t_1$ during which a low test potential, such as +/−20 mV for example, may be applied. A low voltage such as +/−20 mV is below the polarization voltage for the electrochemical cell, and hence the glucose and mediator species remain substantially inactive. Therefore at voltages below the polarization voltage, applicants believe that the resistance of the sample depends mostly on the sample characteristics such as the level of haematocrit and environmental factors such as temperature.

Figure 9A:
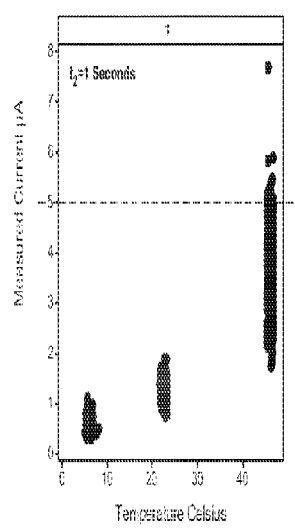
FIG. 9A illustrates a plot of measured current values taken at or prior to a change from a first voltage to a second voltage (e.g., at 1 second or earlier)
Figure 9B:
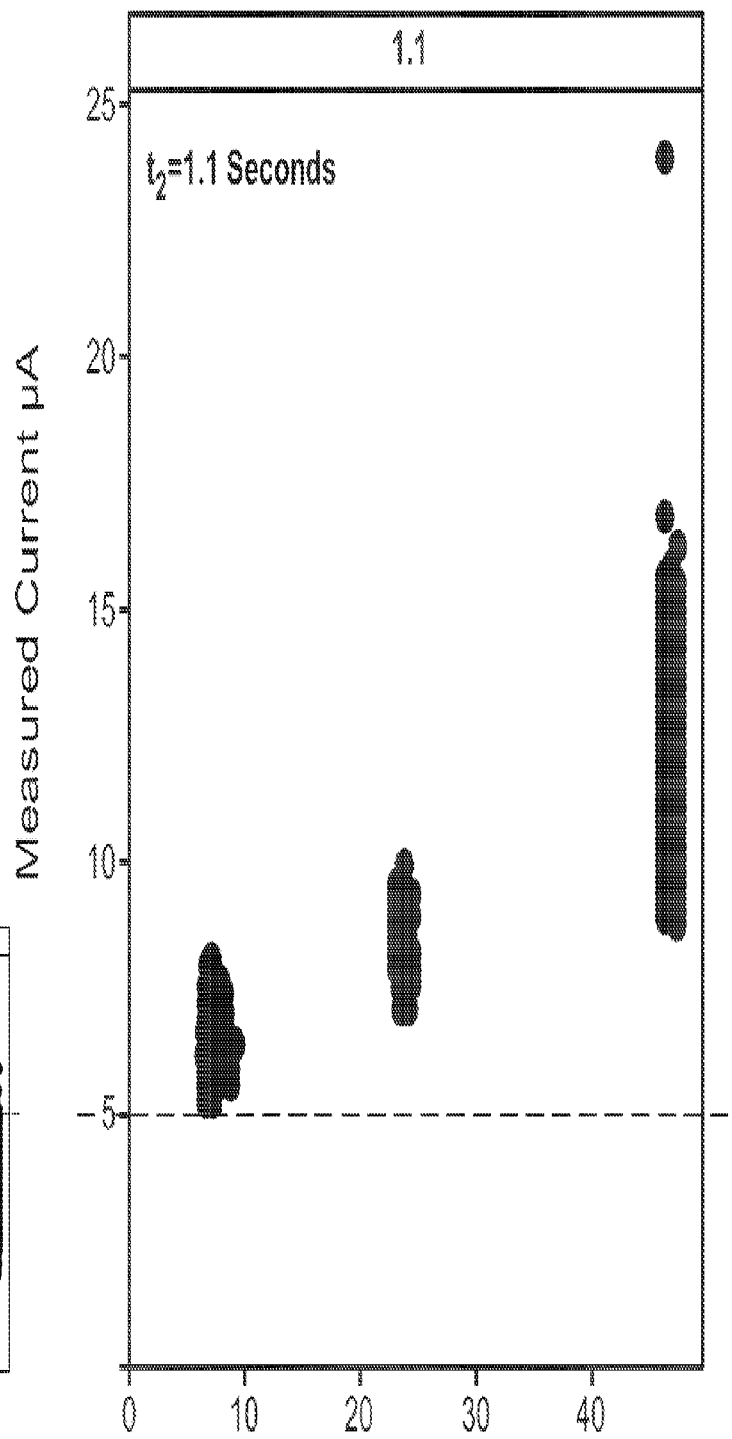
FIG. 9B illustrates a plot of measured current values taken after a change from a first voltage to a second voltage (e.g., at about 1.1 second)

FIG. 9A shows measurements of test current against temperature taken at 1.0 seconds (at or prior to the transition line $T_L$ in FIG. 6B) and FIG. 9B shows measured test currents at about 1.1 seconds (after the transition line $T_L$ in FIG. 6B) into the current transient CT, again using the same temperature conditions (7, 23 and 43° C.) described in relation to FIGS. 7A-7E and 8. FIG. 9A shows a much greater magnitude of the sampled current after the transition line $T_L$ as compared to the magnitude of the sampled current at or prior to the transition line $T_L$. Specifically, FIGS. 9A and 9B show a higher correlation between test current and temperature for measurements at or prior to the transition line $T_L$ ($i_{pb}$ at about 1 second in FIG. 6B) in FIG. 9A, compared to measurements of current taken after the transition line $T_L$, i.e. 0.1 seconds later ($i_{pb}$ in FIG. 6B) at about 1.1 second for FIG. 9B.

EXAMPLE 1

Determination of Bias with No Temperature Compensation

A batch of test strips was tested with over six hundred whole blood samples (see Table 1 below for numbers, n) having three different glucose concentrations (i.e., 73 mg/dL, 250 mg/dL and 500 mg/dL), all with normal hematocrit, e.g., about 42%. The same set of whole blood samples were tested at three different temperatures: 5, 23 and 45 degrees Celsius. The glucose concentration was determined for each data point as described previously using no temperature compensation and using Equation 8 above with ipb=1.1 (i.e., old algorithm) and ipb=1.0 (i.e., new algorithm).

The bias, which is an estimate of the relative error in the glucose measurement, was next calculated for each glucose concentration determined with the old and new algorithms. The bias for each glucose concentration was determined with equations of the form:

$$\text{Bias}_{abs} = G_{calculated} - G_{reference} \quad \text{Eq. 9}$$

for $G_{reference}$ less than 75 mg/dL glucose and $$\text{Bias}_\% = \frac{G_{calculated} - G_{reference}}{G_{reference}} \quad \text{Eq. 10}$$

for $G_{reference}$ greater than or equal to 75 mg/dL glucose where $\text{Bias}_{abs}$ is absolute bias, Bias % is percent bias, $G_{calculated}$ is the glucose concentration determined by the old or new algorithm and $G_{reference}$ is the reference glucose concentration.

Figure 10:
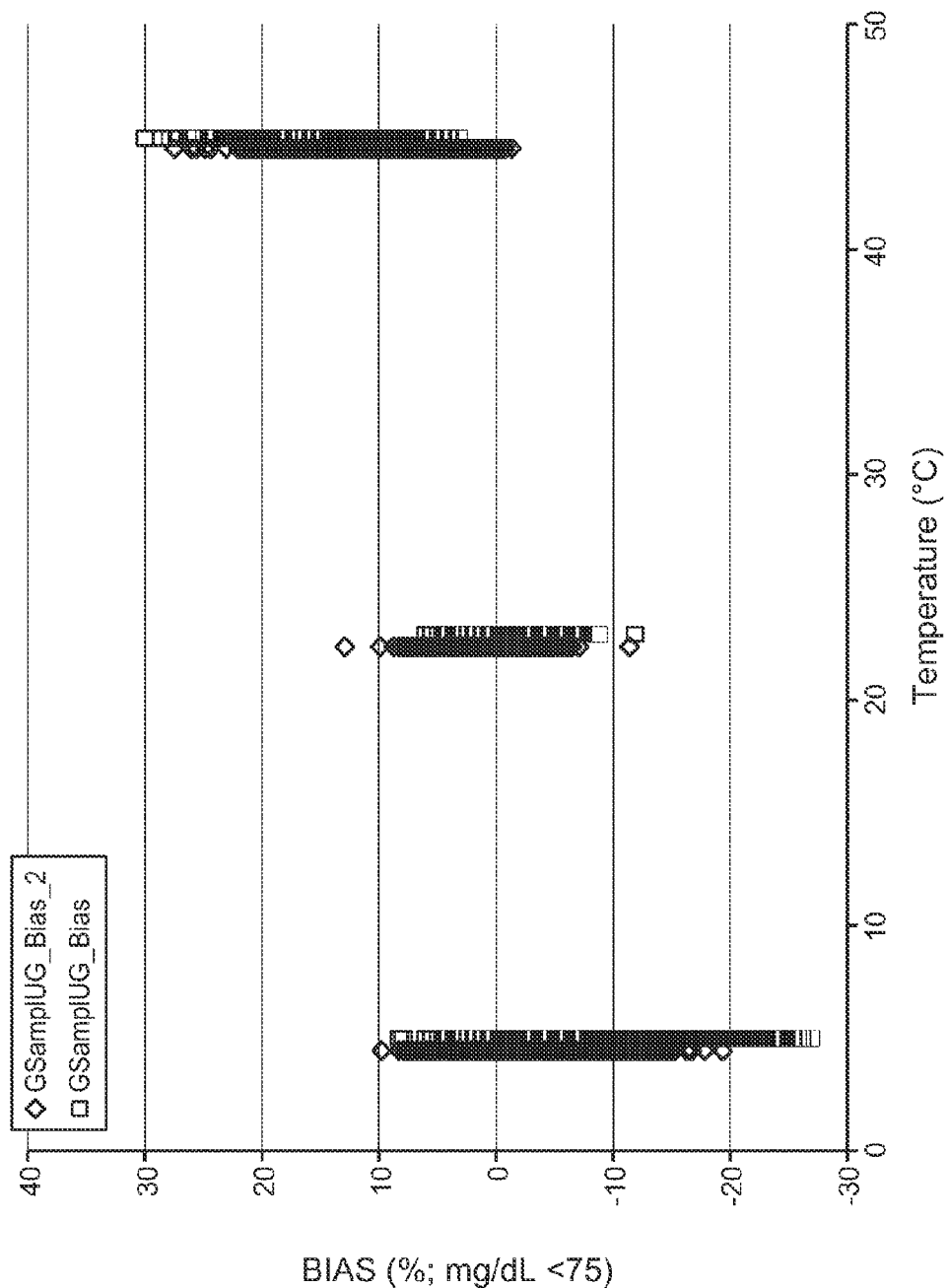
FIG. 10 is a plot of the uncompensated bias to YSI for glucose measurements calculated using the disclosed technique without temperature compensation, compared with the same sample data analyzed with temperature compensation for glucose.

FIG. 10 is a plot of the uncompensated bias to YSI Life Sciences (YSI) standard for glucose measurements calculated using Equations 8 and 8.4 (algorithm without temperature compensation of this application) by measuring $i_{pa}$ at 1.0 seconds (GSampleUG_Bias_2 in FIG. 10), compared with the same sample data analyzed using Equations 8 and 8.2 (algorithm with required temperature compensation of the '899 application) that measures $i_{pb}$ at about 1.1 seconds (SampleUG_Bias in FIG. 10) into the current transient.

As can be seen from the data in FIG. 10, measuring the test current at slightly prior to or before the transition line $T_L$ when the applied voltage is less than 300 mV (at 1.0 second when the applied voltage is about 20 mV) into the transient CT instead of later after the transition line $T_L$ when the applied voltage is at 300 mV (at about 1.1 seconds), for example, provides a significant improvement in the bias, which is especially noticeable at low temperatures. Such an improvement in bias has been achieved by measuring the current $i_{pa}$ (at the applied voltage of less than 300 mV) with the correction factor c, and does not require further modification, for example, of the same manufacturing parameters p, a, b, and Z. In the preferred embodiments, a is approximately 0.192; b is approximately 0.678; p is approximately 0.523, zgr is approximately 2, and scaling or correction factor c is approximately from about 15 to about 25 and most preferably, about 20.

The data from FIG. 10 may also be presented as a percent falling within different ISO (International Standards Organization) bias criteria, as illustrated in Table 1 below.

TABLE 1

Summary of Bias Results

| ISO Bias Criteria | Percent within Bias Criteria for old algorithm (or $i_7$ = 1.1 sec and E2 ~300 mV) | | Percent within Bias Criteria for New algorithm (or $i_7$ = 1.0 sec and E1 ~20 mV) | |
| --- | --- | --- | --- | --- |
| Approx. (%) | % | n | % | n |
| +/−20 | 86.5 | 837 | 96.9 | 747 |
| +/−15 | 72.5 | 719 | 83.2 | 626 |

The data in Table 1 indicates an increase in the percent of data falling within each ISO bias criteria when $i_{pa}$ is measured before the transition line $T_L$, i.e., at 1.0 second. At the ±20% bias, the percentage within the bias criteria is 96.9% without temperature compensation for the presently described technique. In contrast, the technique that utilizes the current resulting from the applied voltage of 300 mV results in the percentage meeting the ±20% bias being less than 90% (about 86.5%) when no temperature compensation was utilized. To improve the data from 86.5% to 95%, temperature compensation had to be made, thereby further complicating the glucose measurement.

Figure 11:
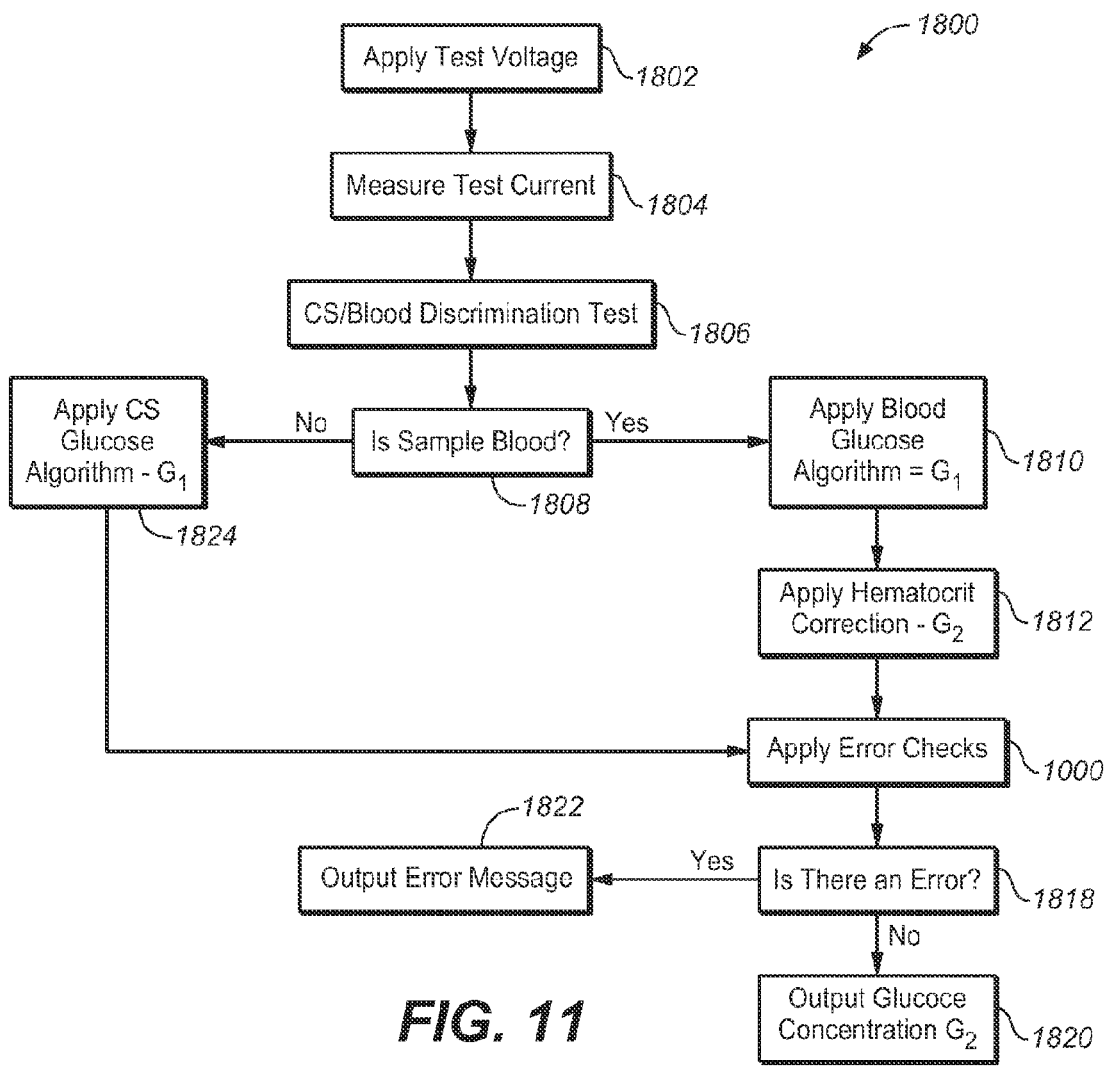
FIG. 11 illustrate an exemplary method of obtaining a blood glucose measurement with the disclosed system.

FIG. 11 illustrates one method of determining a glucose concentration using a flow diagram using the newly discovered techniques described herein. A user can insert test strip 62 into a test meter 10 (which goes into a fluid detection mode) and then apply a sample to the test strip 62. The test meter 10 with its associated circuitry detects the presence of the sample (sample detection not shown for brevity) and applies a test voltage, as shown in step 1802 to cause a transformation of analytes (e.g., glucose), if any, in the blood sample into other chemical products. In response to the test voltage, the test meter 10 measures a test current, as shown in a step 1804. A microprocessor of the test meter can then process the resulting test current values so that an accurate analyte (e.g., glucose) measurement can be determined and displayed.

Another step in the method, as shown in step 1806, can be performing a control solution (CS)/blood discrimination test. As indicated in step 1808, if the CS/blood discrimination test determines that the sample is blood, then method 1800 moves to a series of steps that include: the application of a blood glucose algorithm 1810, hematocrit correction 1812, and error checks 1000; and if the CS/blood discrimination test determines that the sample is CS (i.e., not blood), then method 1800 moves to a series of steps that include: the application of a CS glucose algorithm 1824, and error checks 1000. After performing the error checks 1000, step 1818 can be performed to determine if there are any errors. If there are no errors, then the test meter 10 annunciates (e.g., display, announce or transmit) a glucose concentration, as shown in a step 1820, but if there are errors, then the meter 10 annunciates an error message, as shown in a step 1822. Specific details for each of the steps are shown and described in copending U.S. Patent Application Publication No. 2009/0301899, which are incorporated by reference in their entirety herein this application.

Further, U.S. Patent Application Publication No. 2007/0235347, entitled "Electrochemical Method of Discriminating Control Solution from Blood" and filed on Mar. 31, 2006; U.S. Patent Application Publication No. 2009/0084687, entitled "Systems and Methods of Discriminating Control Solution From a Physiological Sample" and filed on Sep. 28, 2007, and U.S. Patent Application Publication No. 2009/0184004, entitled "System and Method For Measuring an Analyte in a Sample" filed on Jan. 17, 2008, and U.S. Pat. No. 7,749,371, patented Jul. 6, 2010 all of which are hereby incorporated by reference in each of their entirety into this application.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of determining blood glucose concentration with a glucose measurement system that includes a test strip and test meter, the test meter having a microcontroller configured to apply a plurality of test voltages to the test strip and measure a current transient output resulting from an electrochemical reaction in a test chamber of the test strip, the method comprising:
   inserting the test strip into a strip port connector of the test meter to connect at least two electrodes of the test strip to a strip measurement circuit;
   initiating a test sequence after deposition of a sample;
   applying a first voltage to the at least two electrodes of the test strip for a first time interval from the initiation of test sequence to cause a transformation of analytes in the sample;
   switching the first voltage to a second voltage different than the first voltage;
   changing the second voltage to a third voltage different from the first or second voltages;
   measuring a first current output of a current transient from the electrodes during an interval for the switching of the first voltage to the second voltage but prior to a complete changeover to the second voltage;
   measuring a second current output of the current transient from the electrodes after the changing from the second voltage to the third voltage;
   estimating a steady state current output of the current transient after the third voltage is maintained at the electrodes; and
   calculating a blood glucose concentration based on the first, second and steady state current output of the current transient without compensation for temperature on the glucose concentration.

2. A method of determining blood glucose concentration with a glucose measurement system that includes a test strip and test meter, the test meter having a microcontroller configured to apply a plurality of test voltages to the test strip and measure a current transient output resulting from an electrochemical reaction in a test chamber of the test strip, the method comprising:
   inserting the test strip into a strip port connector of the test meter to connect at least two electrodes of the test strip to a strip measurement circuit;
   initiating a test sequence after deposition of a sample;
   applying a first voltage to the at least two electrodes of the test strip for a first time interval from the initiation of test sequence to cause a transformation of analytes in the sample;
   switching the first voltage to a second voltage different than the first voltage;
   changing the second voltage to a third voltage different from the first or second voltages;
   measuring a first current output of a current transient from the electrodes during an interval for the switching of the first voltage to the second voltage but prior to a complete changeover to the second voltage;
   measuring a second current output of the current transient from the electrodes after the changing from the second voltage to the third voltage;
   estimating a steady state current output of the current transient after the third voltage is maintained at the electrodes; and
   calculating a blood glucose concentration based on the first, second and steady state current output of the current transient without compensation for temperature on the glucose concentration with an equation of the form:

$$G_1 = \left(\frac{|i_r|}{|i_l|}\right)^p (a|i_{2CORR}| - zgr);$$

where: $G_1$ is proportional to a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.0}|}{|i_{4.1}| + b|i_5|}\right) i_r$$

where:
   a, b, c, p, zgr comprise manufacturing parameters;
   wherein a is approximately 0.192; b is approximately 0.678; p is approximately 0.523; zgr is approximately 2; and scaling or correction factor c is approximately about 20;
   $i_{4.1}$ is the current measured at about 4.1 seconds after initiation of test sequence;
   $i_5$ is the current measured at about 5 seconds after initiation of test sequence;
   $i_{1.0}$ is the current measured at about 1 second after initiation of test sequence.

3. The method of any one of claim 1 or claim 2, in which the measuring of the first current output comprises measuring a current output of the at least two electrodes at about 1 second after initiation of test sequence.

4. The method of any one of claim 1 or claim 2, in which the measuring of the second current output comprises measuring a current output of the at least two electrodes at about 4.1 seconds after initiation of test sequence.

5. The method any one of claim 1 or claim 2, in which the estimating of the steady state current output comprises measuring a current output of the at least two electrodes at about 5 seconds after initiation of test sequence.

6. A blood glucose measurement system comprising:
   an analyte test strip including:
      a substrate having a reagent disposed thereon;
      at least two electrodes proximate the reagent in test chamber;
   an analyte meter including:
      a strip port connector disposed to connect to the two electrodes;
      a power supply; and
      a microcontroller electrically coupled to the strip port connector and the power supply so that, when the test strip is inserted into the strip port connector and a blood sample is deposited in the test chamber for chemical transformations of glucose in the blood sample, a glucose concentration of the blood sample is determined by the microcontroller without additional temperature compensation for the glucose concentration
   wherein the microcontroller is programmed to deliver a plurality of voltages to the electrodes and calculate the glucose concentration from a current transient output from the electrodes with an equation of the form:

$$G_1 = \left(\frac{|i_r|}{|i_l|}\right)^p (a|i_{2CORR}| - zgr);$$

where: $G_1$ is proportional to a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.0}|}{|i_{4.1}| + b|i_5|}\right)i_r$$

wherein a, b, c, p, zgr comprise manufacturing parameters; a is approximately 0.192; b is approximately 0.678; p is approximately 0.523; zgr is approximately 2; and scaling or correction factor c is approximately about 20;

$i_{4.1}$ is the current measured at about 4.1 seconds after initiation of test sequence;

$i_5$ is the current measured at about 5 seconds after initiation of test sequence; and $i_{1.0}$ is the current measured at about 1 second after initiation of test sequence of blood sample.

7. A blood glucose measurement system to measure a glucose concentration in physiological fluid of a user, the system comprising: a test strip including an electrochemical cell having at least a working electrode and a counter electrode and a reagent layer having a mediator in a test area, the electrodes being connected to corresponding contact pads; and an analyte meter having a microprocessor and a test circuit in connection with a test strip port that electrically connects the contact pads of the test strip so that the meter is configured to apply first, second, and third voltages after deposition of physiological fluid on the electrodes and determine a glucose concentration from measuring a first current output of a current transient from the electrodes during an interval for switching of the first voltage to the second voltage but prior to a complete changeover to the second voltage; measuring a second current output of the current transient from the electrodes after changing from the second voltage to the third voltage; and estimating a steady state current output of the current transient after the third voltage is maintained at the electrodes without any temperature compensation for the glucose concentration.

8. The blood glucose measurement system of claim 7, wherein the first measured current output comprises a current measured prior to 1.1 seconds from the deposition of the physiological sample.

9. The blood glucose measurement system of claim 7, in which the meter is programmed with an equation of the form:

$$G_1 = \left(\frac{|i_r|}{|i_l|}\right)^p (a|i_{2CORR}| - zgr);$$

where: $G_1$ is proportional to a glucose concentration;

$$i_r = \sum_{t=4.4}^{t=5} i(t);$$

$$i_l = \sum_{t=1.4}^{t=4} i(t);$$

$$i_{2(Corr)} = \left(\frac{|i_{4.1}| + b|i_5| - c|i_{1.0}|}{|i_{4.1}| + b|i_5|}\right)i_r$$

wherein a, b, c, p, zgr comprise manufacturing parameters; a is approximately 0.192; b is approximately 0.678; p is approximately 0.523; zgr is approximately 2 and scaling or correction factor c is approximately about 20;

$i_{4.1}$ is the current measured at about 4.1 seconds after initiation of test sequence;

$i_5$ is the current measured at about 5 seconds after initiation of test sequence; and $i_{1.0}$ is the current measured at about 1 second after initiation of test sequence of blood sample.

* * * * *